United States Patent [19]

Wright

[11] Patent Number: 4,663,446

[45] Date of Patent: May 5, 1987

[54] N² (PHENYL SUBSTITUTED) DEOXY GUANOSINE CONTAINING COMPOUNDS

[75] Inventor: George E. Wright, Worcester, Mass.

[73] Assignee: Trustees of the Univ. of Massachusetts, Amherst, Mass.

[21] Appl. No.: 508,483

[22] Filed: Jun. 27, 1983

[51] Int. Cl.⁴ .................... C07H 19/20; C07H 19/173
[52] U.S. Cl. ........................................ 536/28; 536/24
[58] Field of Search ....................... 424/180, 251, 253; 536/23, 24, 26, 27, 28, 29; 544/277, 329

[56] References Cited

U.S. PATENT DOCUMENTS 3,480,613  11/1969  Walton .................................. 536/24
3,936,439   2/1976  Marumoto et al. ................... 536/26
4,267,171   5/1981  Bergstrom et al. ................. 424/180

OTHER PUBLICATIONS

Gutorou et al., Amino Purines, Chem Abstracts 91: 108007a (1979).
Wright et al., Butylanilinouracil: A Selective Inhibiter of . . . HeLa Cell DNA Polymerase Alpha, Chem Abstracts 92:123967c (1980).
Nishimura et al., Optical Rotary Dispension of the Anomeric Nucleosides and Nucleotides, Biochem Biophys Acta 157, B pp. 221-232 (1968).
Bauer, Laboratory Studies on Acyclovir, Chem Abstracts 94:167716r (1980).
St. Clair et al., Inhibition of Cellular Alpha and Virally Induced DNA Polymerases by the Triphosphate of Acyclovir, Chem Abstracts 94:26701v (1980).
Wright et al., Inhibitors of B. Subtilis DNA Polymerase III, 6-Anilinouracils and 6-(Alkylamino)uracils, J Med Chem 23, pp. 34-38 (1980).
Wright et al., Design and Characterization of N²-Arylaminopurines Which Selectively Inhibit . . . Replication-Specific DNA Polymerases . . . , Nucleic Acids Research 10, pp. 4431-4440 (7/24/82) (1982).
Brown et al., Inhibitors of B. Subtilis DNA Polymerases III . . . 6-Anilinouracils, Chem Abstracts 87: 194650b (1977).
Rochowska et al., Inhibitions of Calf Thymus DNA Polymerase Alpha of . . . Cancer Cell Growth by Butylanilinouracil and Butylphenylguanine, Chem Abs 98:245g (1982).

Primary Examiner—Johnnie R. Brown
Attorney, Agent, or Firm—Paul J. Cook

[57] ABSTRACT

New purine compounds having the formula:

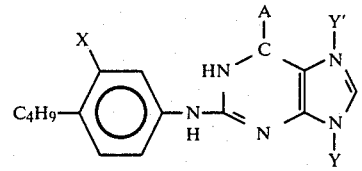

Y and Y'=H,

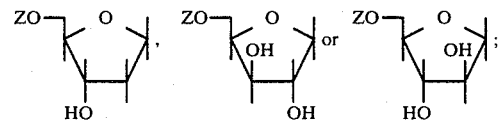

X=H, alkyl, halo;

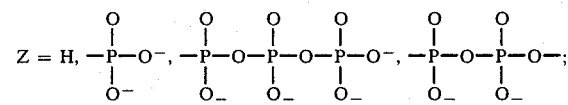

A=O, S, NH₂ are provided. These compounds are useful in treating patients having cancer, since they are potent and selective inhibitors of replicative DNA synthesis in mammalian cells since they inhibit DNA polymerase α.

New purine compounds also are provided having the formula:

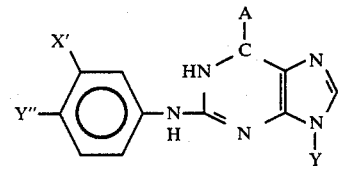

wherein Y, A, Z are as defined above,
X'=C₂H₅ Y''=—CH₃ or

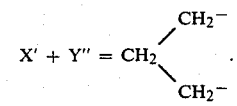

These compounds are useful to prevent bacterial growth since they are potent inhibitors of DNA polymerase III.

New Purine compounds also are provided having the formula:

(Abstract continued on next page.)

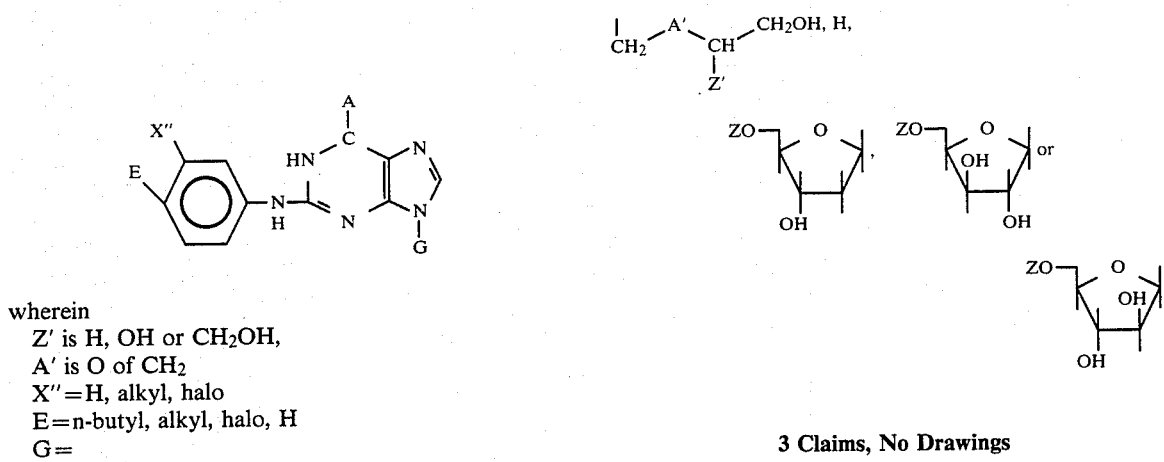
wherein
Z' is H, OH or CH₂OH,
A' is O of CH₂
X″=H, alkyl, halo
E=n-butyl, alkyl, halo, H
G=
3 Claims, No Drawings

N² (PHENYL SUBSTITUTED) DEOXY GUANOSINE CONTAINING COMPOUNDS

BACKGROUND OF THE INVENTION

This invention relates to novel compositions and methods for inhibiting the activity of mammalian DNA polymerase α, bacterial DNA polymerase III or viral-specific DNA polymerases.

Prior to the present invention, 6-substituted uracils of the formula:

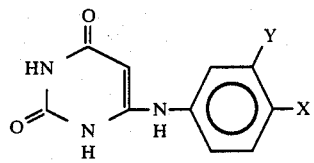

wherein Y is hydrogen and X is p-n-butyl are strong inhibitors against polymerase α but not against *B. subtilis* DNA polymerase III. In contrast, when X or Y is methyl or chlorine, the uracil is a strong inhibitor of *B. subtilis* DNA polymerase III, but has no measurable effect on DNA polymerase α. It is believed that these uracils function by a mechanism that involves the specific pairing of substituents of the uracil moiety with template cytosine and binding of the 6-aryl group and its substituents to the polymerase, thereby sequestering the polymerase in a relatively stable protein: drug template complex.

It would be desirable to provide more potent and/or selective inhibitors of specific polymerases including polymerase α, polymerase III and viral-specific polymerases so that the polymerases in mammalian cells, bacteria and viruses can be specifically inhibited.

SUMMARY OF THE INVENTION

In accordance with this invention, 3 classes of substituted purine compounds are provided which are specific in their effect of inhibiting polymerase α, polymerase III or viral-specific polymerase. The compounds specific for inhibiting polymerase α are defined as follows:

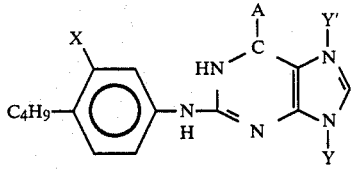

Y and Y'=H,

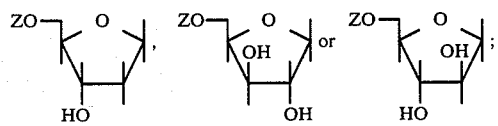

X=H, alkyl, halo;

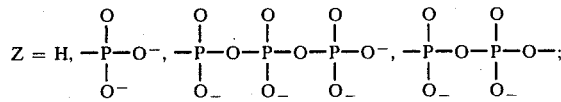

A=O, S, NH₂.

The compounds specific for inhibiting polymerase III are as follows:

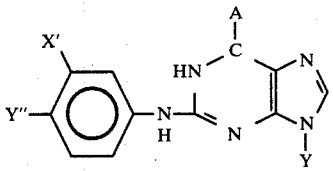

wherein Y, A, Z are as defined above,
X'=C₂H₅
Y''=CH₃ or

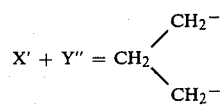

The compounds specific for inhibiting DNA polymerases of viral origin are as follows:

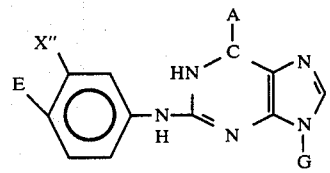

wherein Z' is H, OH or CH₂OH
A' is O of CH₂
X''=H, alkyl, halo
E=n-butyl, alkyl, halo, H
G=

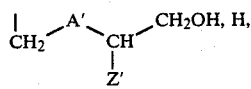

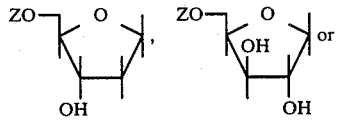

DETAILED DESCRIPTION OF SPECIFIC EMBODIMENTS

The compounds of this invention useful for inhibiting polymerase α are prepared by first reacting 2-chlorohypoxanthine or 2-bromohypoxanthine with p-n-butylaniline to N²-(p-n-butylphenyl)guanine (BuPG).

The reaction can be effected smoothly in boiling aqueous 2-methoxyethanol, which is disclosed by Wright et al, J. Med. Chem. 23, page 34 (1980). The compound BuPG is represented by the formula:

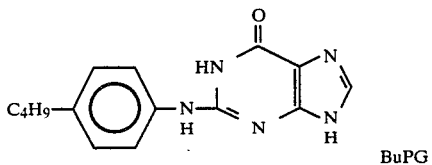

BuPG

In order to produce isomeric BuPG 2'-deoxyribonucleosides, BuPG is silylated with bis[N,O-trimethylsilyl(acetamide)], BSA, in a dry solvent such as dry 1,2-dichloroethane. The silylated base then can be reacted with 1-chloro-3,5-di-p-toluoyl-2-deoxyribofuranose in the presence of trimethylsilyl trifluoromethanesulfonate as the Friedel-Crafts catalyst. The nucleoside mixture then is deblocked such as with sodium methoxide to produce, in addition to other isomers, the 2'-deoxyribonucleoside compound of the formula:

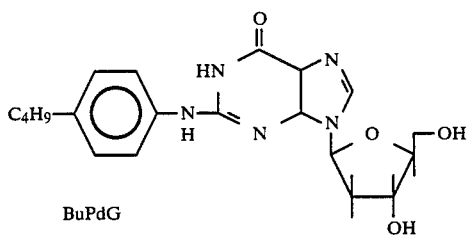

BuPdG

The deoxyribonucleoside can be also produced from reduction of the ribonucleoside, which is produced by silylating the BuPG by the procedure set forth above in dry acetonitrile. Tetra-O-acetylribofuranose and trimethylsilyl trifluoromethanesulfonate are added and the reaction s conducted in boiling acetonitrile. The resultant mixture can be separated such as on a silica gel column. The reactions described for deoxyribonucleoside above are also useful to produce the polymerase III inhibitors when the n-butyl substituent is replaced with 3',4'-trimethylene or 3'-ethyl-4'-methyl. In addition, the corresponding xylonucleosides and arabinonucleosides can be produced when the ribofuranose reactant is replaced with 1-chloro-per-O-acetyl-xylofuranose or 1-chloro-per-O-benzylarabino-furanose. Furthermore, the corresponding monophosphate (such as BuPdGMP), diphosphate (such as BuPdGDP) and triphosphate (such as BuPdGTP) derivatives can be produced by reaction of the nucleoside with phosphoryl chloride, and subsequent reaction of the monophosphate with 1,1-carbonyl-diimidazole and pyrophosphate. Furthermore, the corresponding antiviral acyclonucleoside can be produced when the ribofuranose is replaced with 2-acetoxyethyl bromomethyl ether, 3,4-(isopropylidinedioxy)-1-bromobutane or 1,3-dibenzyl-2-acetoxymethylglycerol.

The compounds are useful in therapeutic treatment of patients afflicted with cancer, bacterial infection or viral infection. It can be administered either alone or in combination with pharmaceutically acceptable carriers. The proportion of active ingredient to carrier is determined by the solubility and chemical nature of the compound, chosen route of administration and standard pharmaceutical practice. The active compound can be administered orally, parenterally or intravenously. For example, the active compound can be administered in tablet form with such excipients as lactose, sodium citrate, calcium carbonate or dicalcium phosphate. Various disintegrants such as starch, alginic acid or certain complex silicates together with lubricating agents such as magnesium sterate, sodium aryl sulfate or talc can be utilized. For oral administration in capsule form, suitable materials include lactose in high molecular weight polyethylene glycols. When utilizing aqueous suspension, the active compounds are combined with the emulsifying and/or suspending agents. Liquid carriers can be employed such as ethanol, water, propylene glycol, glycerine, glycine or the like. For parenteral administration, solutions of the active compound in combination with other solutes such as glucose or saline can be utilized. Such aqueous solutions should be suitably buffered in order to render them isotonic. The dosage required to obtain effective inhibition of cancer, bacterial or viral growth will depend primarily on the condition of the patient being treated. A general procedure comprises small dosages being administered initially with a gradual increase in dosage until an optimal level is determined for a particular patient. When the active compound is administered orally, generally larger quantities of the active compound will be required to produce the same level of inhibition of cancer, or bacterial or viral growth as produced by a smaller quantity administered parenterally. In general, from about 2 mg to about 30 mg, preferably between about 2 mg and about 15 mg, of the active compound per kilogram of body weight administered in single or multiple dosage usits effectively prevents growth of cancer cells, bacteria or virus.

The preferred compounds of this invention are as follows:

$N^2$-(p-n-butylphenyl)guanine, BuPG
$N^2$-(p-n-butylphenyl)deoxyguanosine, BuPdG
$N^2$-(p-n-butylphenyl)deoxyguanosine 5'-phosphate, BuPdGMP
$N^2$-(p-n-butylphenyl)deoxyguanosine 5'-diphosphate, BuPdGDP
$N^2$-(p-n-butylphenyl)deoxyguanosine 5'-triphosphate, BuPdGTP 2-(p-n-butylanilino)adenine, BuAA
$N^2$-(p-n-butylphenyl)-6-thioguanine, BuPTG
$N^2$-(3'-ethyl-4'-methylphenyl)guanine, EMPG
$N^2$-(3',4'-trimethylenephenyl)guanine, TMPG
$N^2$-(3'-ethyl-4'-methylphenyl)deoxyguanosine, EMPdG
$N^2$-(3'-ethyl-4'-methylphenyl)deoxyguanosine, 5'-phosphate, EMPdGMP
$N^2$-(3'-ethyl-4'-methylphenyl)deoxyguanosine, 5'-diphosphate, EMPdGDP
$N^2$-(3'-ethyl-4'-methylphenyl)deoxyguanosine, 5'-triphosphate, EMPdGTP It is to be understood that the active compounds of this invention can be administered either as the compound or in any other pharmaceutically acceptable form such as the sodium salt form or any other salt form.

The following examples illustrate the present invention and are not intended to limit the same.

Melting points were determined on a Mel-temp apparatus and are uncorrected. Ultraviolet spectra were determined with a Beckman Model 25 spectrophotometer. Nuclear magnetic resonance spectra were obtained on Perkin Elmer R-12B (60 MHz) or Bruker WM-250

(250 MHz) spectrometers, both operating in the FT mode. Solvents were dried by standard methods; anhydrous acetonitrile from MCB was used without further purification. Elemental analyses (C,H,N) were done by Schwarzkopf Microanalytical Laboratories, Woodside, NY. Thin-layer chromatography was performed with Merck Kieselgel 60 F-254 analytical plates. Column chromatography was done with Merck Kieselgel 60 (40-60 μm).

EXAMPLE I

$N^3$-(p-n-butylphenyl)guanine (BuPG)

A stirred solution of 2-bromohypoxanthine (10.8 g, 50 mmol) and p-n-butylaniline (23.5 mL, 150 mmol) in a mixture of 2-methoxyethanol (300 mL) and water (100 mL) was heated at reflux. After 2.5 h, the mixture was chilled in an ice bath, and the fine precipitate was filtered, washed with concentrated aqueous ammonia (80 mL) and methanol (3×25 mL). The product was purified by dissolving the slightly yellow precipitate in hot N sodium hydroxide (300 mL) and treatment with activated charcoal. The hot mixture was filtered, acidified with glacial acetic acid and chilled. The product was isolated by filtration, washed with methanol and dried over phosphorus pentoxide to yield 12.0 g (85%) of fine colorless crystals, identical with an authentic sample. NMR (250 MHz; Me$_2$SO-d$_6$) 10.45 δ(s, 1-H), 8.60 δ(s, 2-NH), 8.00 δ(s, 8-H), 7.50 δ(d, J+8.5 Hz, 2',6'-H), 7.14 δ(d, J=8.5 Hz, 3',5'-H), 2.55 δ(t, CH$_2$), 1.56 δ(quin, CH$_2$), 1.33 δ(sext, CH$_2$), 0190 δ(t, CH$_3$).

EXAMPLE II

$N^2$-(p-n-Butylphenyl)-9-(2-deoxy-β-D-ribofuranosyl)-guanine (BuPdG) and its 7-β and 7-α Isomers A solution of BuPG (1.70 g, 6 mmol) in 1,2-dichloroethane (25 mL) was treated with BSA (10.5 mL, 42 mmol) and allowed to stand at room temperature for 1 h. A solution of 1-chloro-3,5-di-p-toluoyl-2-deoxyribofuranose (1.94 g, 5 mmol) in 1,2-dichloroethane (20 mL) and a solution of TMSTF (1.56 g, 7 mmol) in benzene (5 mL) were added to the silylated BuPG solution. After standing for 2 h at room temperature, the solution was heated to boiling and brought to room temperature. The solution was poured into a mixture of saturated aqueous sodium bicarbonate (150 mL) and chloroform (150 mL). The cloudy biphasic mixture was filtered and the precipitate was washed with chloroform. The filtrate and washings were combined and the organic phase was separated. The organic phase was washed with water (3×100 mL), dried over anhydrous sodium sulfate and the solvent removed under vacuum. The remaining syrup was triturated with cold ethanol (50 mL) and the solid was collected by filtration to give 2.35 g (67%) of nucleoside mixture. The solid was treated with sodium methoxide (230 mg Na in 120 mL methanol) at 50°-60° C. for 1 h, and the solution was neutralized with glacial acetic acid. Silica gel (20 g) was impregnated with this mixture and, after evaporation of methanol, was placed on top of a silica gel column (24×4.5 cm). The column was washed with chloroform (1.2 L) to remove nonpolar components, and nucleosides were eluted in 15 mL fractions by a step gradient of methanol in chloroform containing 0.5% acetic acid: 10% methanol (3.6 L), 20% methanol (2.5 L) and 25% methanol (2.0 L).

Fractions 13-44 were combined and the solvents evaporated. The resulting solid was dissolved in a hot mixture of ethanol (2 mL) and aqueous ammonia (5 ml). After standing at room temperature for 3 days, the colorless crystals were collected by filtration to give 312 mg (15.6%) of 7-β isomer, mp 184°-185° C. UVλ$_{max}$ (H$_2$O) 263 (ε11300), (pH 2) 263 (ε13100), and (pH 12) 266 nm (ε14700).

Anal. Calcd for C$_{20}$H$_{25}$N$_5$O$_4$.0.25H$_2$O: C, 59.48; H, 6.26; N, 17.35. Found: C, 59.5; H, 6.09; N, 17.25.

Fractions 73-100 contained a solid which was dissolved in methanol and, after filtration, was diluted with water and slowly evaporated to give a cloudy solution. Slow cooling produced colorless needles of 7-α isomer (110 mg, 5.5%), mp 193°-195° C. UVλ$_{max}$ (H$_2$O) 264 (ε14600), (pH 2) 265 (ε18000), and (pH 12) 267 (ε20300) and 239 nm (ε13900).

Anal. Calcd for C$_{20}$H$_{25}$N$_5$O$_4$.0.67H$_2$O: C, 58.39; H, 6.41; N, 17.03. Found: C, 58.29; H, 6.11; N, 16.80.

Fractions 113-144 contained a solid which was crystallized from ethanol-aqueous ammonia to give the BuPdG as colorless crystals (368 mg, 18.4%), mp 196°-197° C. UVλ$_{max}$ (H$_2$O) 273 (ε19800), (pH) 272 (ε20300), and (pH 12) 278 (ε23500) and 231 nm (ε16700).

Anal. Calcd for C$_{20}$H$_{25}$N$_5$O$_4$.0.25H$_2$O; C, 59.48; H, 6.26; N, 17.35. Found: C, 59.70; H, 6.27; N, 17.16.

EXAMPLE III

$N^2$-(p-n-Butylphenyl)-9-(β-D-2,3,5-tri-O-acetyl-ribofuranosyl)guanine and its 7-α isomer A solution of BuPG (8.15 g, 28.8 mmol) in anhydrous acetonitrile (100 mL) was treated with BSA (36 mL, 144 mmol). After 1 h at room temperature, a solution of tetra-O-acetylribofuranose (7.63 g, 24 mmol) in acetonitrile (100 mL) was added, followed by TMSTF (6.32 mL, 34.8 mmol). After heating at reflux for 2 h, an additional portion of BSA (7 mL, 28 mmol) was added, and the reaction mixture was heated at reflux for 7 h. The reaction mixture was concentrated under vacuum, the residue dissolved in chloroform (300 mL) and this solution was poured into water (300 mL). The biphasic mixture was filtered to remove unreacted BuPG, and the organic phase was separated, washed with water (3×150 mL), dried over anhydrous sodium sulfate and evaporated to dryness. The residue was crystallized from ethanol (100 mL) to give 9.01 g (69%) of the 9-β isomer as colorless crystals, mp 241°-243° C.

Anal. Calcd for C$_{26}$H$_{31}$N$_5$O$_8$: C, 57.67; H, 5.37; N, 12.94. Found: C, 57.96; H, 5.96; N, 12.90.

The filtrate from crystallization of 6 was evaporated to dryness and chromatographed on a silica gel column (30×2.5 cm). Elution with 0.1% methanol in chloroform (1.5 L) gave the 7-β isomer as a foam (1.4 g, 11%). This compound was homogeneous by tlc and was identified by its nmr spectrum.

EXAMPLE IV

$N^2$-(p-n-Butylphenyl)-9-(β-D-ribofuranosyl)guanine (BuPGR) and its 7-β isomer The O-acetyl derivatives were deblocked by treatment with a mixture of equal volumes of concentrated aqueous ammonia and ethanol for 3 days. The resulting gels were heated and, after cooling, the solutions deposited fine colorless crystals which were collected by filtration and dried over phosphorus pentoxide in vacuo.

The 9-β isomer (9.01 g) gave 6.76 g (98%) of BuPGR, mp 213°-223° C. (dec.).

Anal. Calcd for $C_{20}H_{25}N_5O_5 \cdot 0.5H_2O$: C, 56.60; H, 6.13; N, 16.50. Found: C, 56.46; H, 6.02; N, 16.60.

The 7-β isomer (1.19 g) gave 900 mg (99%) of 7-β-BuPRG, dec. 225° C.

Anal. Calcd for $C_{20}H_{25}N_5O_5$: C, 57.83; H, 6.02; N, 16.87. Found: C, 57.62; H, 6.01; N, 16.57.

EXAMPLE V $N^2$-(p-n-Butylphenyl)-9-β-D-(3',5'-(tetraisopropyl-disiloxane-1,3-diyl)ribofuranosyl)guanine (TIPS-BuPGR)

BuPGR (6.23 g, 15 mmol) was dried by coevaporation with pyridine (2×30 mL). The resulting syrup was dissolved in pyridine (65 mL) and treated with tetraisopropyl-1,3-dichlorodisiloxane (5.25 g, 16.5 mm91), and the mixture stood overnight at room temperature. An additional 0.7 mL of reagent was added and the reaction stood for 4 h. The solvent was removed in vacuo, the residual syrup was extracted with water (4×200 mL). The organic phase was separated by filtration through phase separator, dried over anhydrous sodium sulfate, and the solvent evaporated. The resulting foam was chromatographed on a silica gel column (50×4.5 cm) in a step-gradient of methanol in chloroform: 1% (2 L), 2% (4 L) and 4% (5 L). Fractions containing the product were collected and evaporated to dryness. The colorless foam of TIPS-BuPGR (8 g, 81%) was dried over phosphorus pentoxide in vacuo and used without purification in the next step. NMR (60 MHz; Me$_2$SO-d$_6$) 7.87 δ(s, 8-H), 5.77 δ(s, H-1'), 1.04 δ(s, SiCH(CH$_3$)$_2$).

EXAMPLE VI $N^2$-(p-n-Butylphenyl)-9-β-D-(2'(imidazolethiocarbonyl)-3',5'-(tetraisopropyldisiloxane-1,3-diyl)-ribofuransyl)guanine (Im-TIPS-BuPGR)

TIPS-BuPGR (1.98 g, 3 mmol) dissolved in dimethylformamide (50 mL) was treated with 1,1'-thiocarbonyl-diimidazole (1.33 g, 7.5 mmol). After 4.5 h at 35° C., the reaction mixture was brought to room temperature and the solvent was removed in vacuo. The residue was dissolved in chloroform (200 mL) and washed with water (6×50 mL). The chloroform layer was filtered through a phase separator, dried over anhydrous sodium sulfate, and evaporated. The residue was crystallized from ethanol to give 1.91 g (83%) of Im-TIPS-BuPGR, mp 237°–240° (dec.). NMR (60 MHz; Me$_2$SO-d$_6$) 8.58, 7.89 and 7.10 (imidazole H), 7.89 δ(s, 8-H), 6.35–6.47 δ(m, H-1' and H-2'), 1.04 δ(s, SiCH(CH$_3$)$_2$).

EXAMPLE VII $N^2$-(p-n-Butylphenyl)-9-β-D-(2'-deoxy-3',5'-(tetraisopropyldisiloxane-1,3-diyl)ribofuranosyl)guanine (TIPS-BuPdG)

To a solution of Im-TIPS-BuPGR (1.9 g, 2.48 mmol) in boiling dry toluene (20 mL) was added dropwise a mixture of tri-n-butyltin hydride (1.74 g, 9.88 mmol) and 2,2'-azobis(2-methylporpionitrile) (270 mg) in dry toluene (20 mL) over 1 h. After an additional 2 h at reflux, the solvent was evaporated in vacuo, and the residue was dissolved in chloroform and chromatographed on a silica gel column (40×4.5 cm). The column was washed with chloroform (1 L) and 1% methanol in chloroform (2 L). The product was crystallized from methanol to give 1.46 g (92%) of TIPS-BuPdG, mp 224°–226° C. NMR (60 MHz, Me$_2$SO-d$_6$) 7.92 δ(s, H-8), 6.19 δ(dd, H-1'), 1.04 δ(s, SiCH(CH$_3$)$_2$).

Anal. Calcd for $C_{32}H_5N_5O_5Si_2 \cdot CH_3OH$: C, 58.67; H, 8.15; N, 10.37. Found: C, 58.75; H, 7.94; N, 10.57.

EXAMPLE VIII $N^2$-(p-n-Butylphenyl)-9-β-D-(2'-deoxyribofuranosyl)-guanine (BuPdG)

A M solution of tetrabutylammonium fluoride in tetrahydrofuran (2 mL) was added dropwise to a solution of 12 (2.08 g, 3.24 mmol) in tetrahydrofuran (20 mL), and the reaction was followed by TLC. After 2 h, the mixture was evaporated, and the residue was dissolved in ethanol and passed through a column filled with Dowex 50W×4, pyridinium form. Silica gel (30 g) was coated with the mixture and placed on top of a column of silica gel (4.5×20 cm). The column was washed with chloroform (1 L) and the product was eluted with mixtures of 2% methanolic boric acid and chloroform (1:4 and 3:7, v/v). Fractions containing the product were evaporated, and the residue coevaporated with methanol to remove boric acid. Crystallization by slow evaporation from ethanol-aqueous ammonia gave 1.13 g (87.4%) of BuPdG, mp 196°–197°, identical with that obtained from direct synthesis.

EXAMPLE IX $N^2$-(p-n-Butylphenyl)-2'-deoxyguanosine 5'-phosphate (BuPdGMP)

Phosphoryl chloride (150 L, 1.64 mmol) was added to a cold solution of BuPdG (399 mg, 1 mmol) in trimethyl phosphate (6 mL). The mixture was kept at 0°–3° C. during 3 h and at −20° C. overnight. An additional portion of phosphoryl chloride (100 L, 1.1 mmol) was added and, after 5 h at 0°–5° C., cold water (15 mL) was poured into the reaction mixture. The thick slurry was neutralized with triethylamine, and the slightly basic solution was diluted with water to a total volume of 250 mL and applied on a DEAE-cellulose column (20×2.5 cm). Elution was carried out in a linear gradient of 0.05–0.50M ammonium bicarbonate (1 L:1 L) during 16 h at a flow rate of 2 mL/min. Fractions 56–116 (13 mL each) containing desired product were combined and evaporated to dryness. The residue was dissolved in several mL of water and evaporated several times with triethylamine and finally with ethanol to dryness. Ths solid triethylammonium salt was dissolved in water and passed through 15 mL of Dowex 50W×8, ammonium form. The eluate was lyophilized to give the ammonium salt 18, 340 mg (66%), contaminated with a side-produce (5%), possibly the 3',5'-diphosphate of 3. The crude produce was purified by chromatography on a silica gel column (25×2.5 cm) with the solvent 2-propanol:concentrated/ammonia:water (7:2:1). Fractions 6–35 (12 mL each) containing pure BuPdGMP were combined and evaporated. The product was converted into its ammonium salt and lyophilized. The recovery of BuPdGMP after purification was 94%. UV$_{max}$ (H$_2$O) 276 (ε17300), (pH 1) 276 (ε16500) and (pH 13) 282 nm (ε19700). Anal. Calcd. for $C_{20}H_{32}N_7O_7P$: P, 6.04%. Found: P, 6.09%.

EXAMPLE X $N^2$-(p-n-Butylphenyl)-2'-deoxyguanosine 5'-triphosphate (BuPdGTP)

BuPdGMP (140 mg, 0.27 mmol) was converted to its tributylammonium salt by passing an aqueous solution through Dowex 50W×8, pyridinium form, and subsequently by coevaporation of the eluate with tributylamine (130 L, 0.54 mmol). The residue was dissolved in a small volume of water and lyophilized. A suspension of the dry substrate in hexamethylphosphoramide (1.5 mL) was treated with 1,1'-carbonyl-diimidazole (203 mg, 1.25 mmol). After 5 min, a clear solution was obtained, and the reaction was quenched after 4.5 h by the addition of 175 L of methanol. TLC showed complete conversion of BuPdGMP into its imidazolyl derivative. A solution of tetra(tributylammonium)pyrophosphate, prepared from tetrasodium pyrophosphate (588 mg, 1.25 mmol), in hexamethylphosphoramide (10 mL) was added dropwise with stirring. The mixture was kept during 24 h at room temperature. The reaction mixture was poured onto 40 g of ice and the solution was applied to a DEAE-cellulose column, bicarbonate form (25×4.4 cm). Elution was carried out in a linear gradient of triethylammonium bicarbonate, pH 7.8, 0.5–0.50M, during 24 h at a flow rate of 4 mL/min. Fractions 102–117 (16 mL each) contained BuPdGMP, fractions 348–374 contained BuPdGDP, and fractions 384–436 contained the major product, BuPdGTP. The fractions containing BuPdGTP were combined and evaporated. The product was converted to its ammonium salt and lyophylized to give 90 mg (47%) of BuPdGTP. UV$_{max}$ (H$_2$O) 276 ($\epsilon$17700), (pH 1) 276 ($\epsilon$17400) and (pH 13) 282 nm ($\epsilon$20500). Anal. Calcd. for C$_{20}$H$_{40}$N$_9$O$_{13}$P$_3$: P, 13.15%. Found: P, 12.40%.

Fractions containing BuPdGDP were treated as above. The yield of BuPdGDP as the ammonium salt was 7 mg (4.3%). UV$_{max}$ (H$_2$O) 276 ($\epsilon$18600), (pH 1) 276 ($\epsilon$18100) and (pH 13) 282 nm ($\epsilon$20700). Anal. Calcd. for C$_{20}$H$_{36}$N$_8$O$_{10}$P$_2$: P, 10.16%. Found: P, 10.37%.

EXAMPLE XIII

This example illustrates the inhibition of polymerase with the compounds of this invention.

Polymerase α Inhibitors

| Drugs | Drug Concentration in Micromolar Causing Half-Maximal Inhibition of DNA Polymerase α From: | |
|---|---|---|
| | Chinese hamster ovary cells | HeLa (human) cells |
| BuPG | 4.8 | 10.0 |
| BuPdG | 10.0 | 2.3 |
| BuPdGMP | .52 | (not done) |
| BuPdGDP | .014 | (not done) |
| BuPdGTP | .005 | .001 |

| Drugs | Micromolar Concentration | Percent Inhibition of Activity of DNA Polymerase α From: | |
|---|---|---|---|
| | | Chinese hamster ovary cells | HeLa (human) cells |
| BuPG | 100 | — | 64 |
| BuPG | 200 | 55 | — |
| BuAA | 100 | — | 52 |
| BuAA | 200 | 67 | — |
| BuPTG | 100 | — | 62 |
| BuPTG | 200 | 72 | — |

| Cell line and type | Percent Inhibition of Human Cell Growth in Cultures by 50 Micromolar Concentrations of: | | |
|---|---|---|---|
| | BuPG | BuPdG | 7β-BuPdG |
| E-14, human lung cancer | 89 | 47 | 81 |
| HZB, human lung cancer | 62 | 13 | 12 |
| F1Wt178, transformed fibroblasts | 85 | 14 | 36 |
| F1W176, normal fibroblasts | 35 | not done | not done |
| F1Wp, normal fetal fibroblasts | 0 | 24 | 0 |

Polymerase III Inhibitors

| Drug | Micromolar Concentration of Drug Causing Half-Maximal Inhibition of DNA Polymerase III from *Bacillus subtilis*: |
|---|---|
| EMPG | 2 |
| TMPG | 5 |

Viral Polymerase Inhibitors

| Viral DNA Polymerase | Micromolar Concentration of BuPdGTP Causing Half-Maximal Inhibition of Polymerase: |
|---|---|
| Vaccinia | 10 |
| Herpes simplex, Type I | 4 |
| Herpes simplex, Type II | 4 |

I claim:

1. A compound capable of inhibiting the activity of DNA polymerase having the formula:

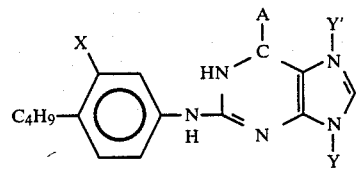

wherein X=H, alkyl, or halo;
Y and Y'=

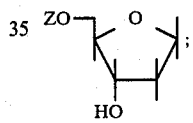

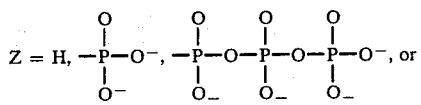

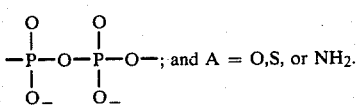

2. A compound capable of inhibiting the activity of DNA polymerase III having the formula:

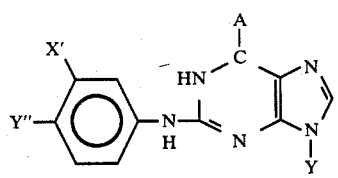

wherein Y=H, or

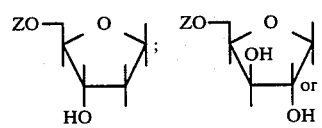

-continued

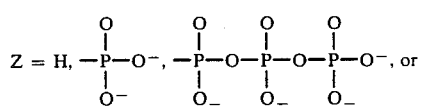

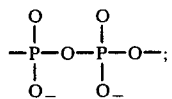

A = O, S, NH₂;

X' = C₂H₅;

Y" = —CH₃ or

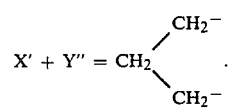

3. A compound capable of inhibiting the activity of viral DNA polymerase having the formula:

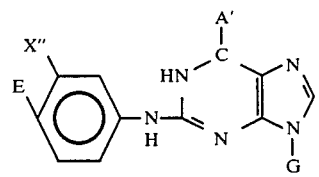

wherein
A' is O or NH₂;
X" = H, alkyl, halo;
E = alkyl, halo, H wherein E and X" are not H simultaneously

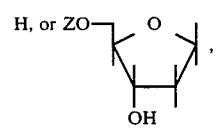

wherein Z' is H, OH, or CH₂OH,

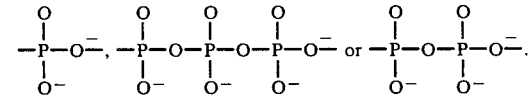

and wherein Z = H, $$-\overset{O}{\underset{O^-}{P}}-O^-, \quad -\overset{O}{\underset{O^-}{P}}-O-\overset{O}{\underset{O^-}{P}}-O-\overset{O}{\underset{O^-}{P}}-O^- \text{ or } -\overset{O}{\underset{O^-}{P}}-O-\overset{O}{\underset{O^-}{P}}-O^{\underline{\phantom{-}}}.$$

* * * * *